(12) United States Patent
Chen

(10) Patent No.: US 6,928,317 B2
(45) Date of Patent: Aug. 9, 2005

(54) HEART RATE TRANSMITTER

(76) Inventor: Tong-Pie Chen, 10Fl-3, No. 379, Jungshan Rd., Sanchung City, Taipei Hsien (TW)

(*) Notice: Subject to any disclaimer, the term of this patent is extended or adjusted under 35 U.S.C. 154(b) by 267 days.

(21) Appl. No.: 10/317,182

(22) Filed: Dec. 12, 2002

(65) Prior Publication Data

US 2004/0116818 A1 Jun. 17, 2004

(51) Int. Cl.$^7$ ............................................. A61B 5/0402
(52) U.S. Cl. ...................................................... 600/509
(58) Field of Search ................................. 600/509, 519, 600/520, 523, 384, 386, 390, 393, 503; 607/9; D24/167, 168, 186, 187

(56) References Cited

U.S. PATENT DOCUMENTS

| | | | | |
|---|---|---|---|---|
| 4,809,700 A | * | 3/1989 | Castelli | 600/384 |
| 5,471,983 A | * | 12/1995 | Magnus | 600/390 |
| 5,778,880 A | * | 7/1998 | Chen | 600/509 |
| 6,728,577 B2 | * | 4/2004 | Minogue et al. | 607/48 |
| D492,783 S | * | 7/2004 | Lax | D24/167 |
| D492,999 S | * | 7/2004 | Lax | D24/167 |

* cited by examiner

Primary Examiner—Jeffrey R. Jastrzab
(74) Attorney, Agent, or Firm—Rabin & Berdo, P.C.

(57) ABSTRACT

A heart rate transmitter comprising a strap and a body. The strap is in long belt shape, a hole is in the center of the strap, a conducting rubber plate each is on both ends of the hole, a contacting tip stretches out from the conducting rubber plate to the inner side of the hole. The body is installed inside the hole of the strap; two contacting points are on both ends of the body. When the body is inserted into the hole of the strap, two contacting points are pressed to contact the contacting tips of the conducting rubber plate inside the hole of the strap; the conducting rubber plate contacts human body to measure the heartbeat rate.

7 Claims, 7 Drawing Sheets

HEART RATE TRANSMITTER

BACKGROUND OF THE INVENTION

I. Field of the Invention

This invention relates generally to a heart rate transmitter and, more specifically, to a heart rate transmitter that users can put the transmitter body into the strap, the two contacting points on both ends of the body can contact firmly onto the contacting tip on the end of the conducting rubber plate of the strap, such scheme can avoid the inconvenience and troublesome of application of tools to assemble.

II. Description of the Prior Art

Heretofore, it is known that a prior heart rate transmitter, as shown in FIG. 6, is composed of a base shell (a) with two conducting plate (b) on top of both ends, a circuit board (c) is installed on top of the base shell (a); two conducting spring (c1) are on the bottom of the circuit board (c) to press on the conducting plate (b); a left strap (d1) and a right strap (d2) are on both ends of the base shell (a), a conducting rubber plate (e) each is fixed on the left strap (d1) and the right strap (d2), on one end of the conducting rubber plate (e) is pressed on the conducting plate (b); the top shell (f) covers on top of the base shell (a) to have the conducting rubber plate (e) of bottom of the left strap (d1) and the right strap (d2) contacting conducting spring (c1) on bottom of the circuitry board by conducting plate (b), as shown in FIG. 7.

The assembly procedure of the known prior heart rate transmitter is to have the conducting plate (b) placed on both end of the base shell (a) first, fix the circuit board (c) on the bottom of the base shell (a) with screw (g), then install the left strap (d1) and the right strap (d2) on top of the conducting plate (b), finally assemble the top shell (f) on top of the base shell (a), the conducting rubber plate (e) on the bottom of can contact the conducting plate (b) through conducting spring (c1) on the bottom of the circuit board (c). Such procedure is not very convenient and has to apply many screws to fix all the components together; the manufacturing cost is higher to reduce the market competition.

The conducting rubber plate (e) is in plain, flat shape, one end can be pressed by the top shell (f) onto the conducting plate (b), however the left strap (d1) and the right strap (d2) are installed between the base shell (a) and the top shell (f), therefore when the left strap (d1) and the right strap (d2) swing up and down might cause the conducting rubber plate (e) under the left strap (d1) and the right strap (d2) not able to contact firmly on the conducting plate (b), this condition causes bad connection and can not transmit correct signals.

SUMMARY OF THE INVENTION

It is therefore a primary object of the invention to provide a heart rate transmitter comprising a strap and a body. Users can press the body into the strap, the two contacting points on both ends of the body can contact firmly onto the contacting tip on the end of the conducting rubber plate of the strap, such scheme can avoid the inconvenience and troublesome of application of tools to assemble.

In order to achieve the objective set forth, a heart rate transmitter in accordance with the present invention comprises a strap and a body. The strap is in long belt shape, a hole is in the center of the strap, a conducting rubber plate each is on both ends of the hole, a contacting tip stretches out from the conducting rubber plate to the inner side of the hole. The body is installed inside the hole of the strap; two contacting points are on both ends of the body. When the body is inserted into the hole of the strap, two contacting points are pressed to contact the contacting tips of the conducting rubber plate inside the hole of the strap; the conducting rubber plate contacts human body to measure the heartbeat rate.

BRIEF DESCRIPTION OF THE DRAWINGS

The accomplishment of the above-mentioned object of the present invention will become apparent from the following description and its accompanying drawings which disclose illustrative an embodiment of the present invention, and are as follows.

DESCRIPTION OF THE PREFERRED EMBODIMENT

Figure 1:
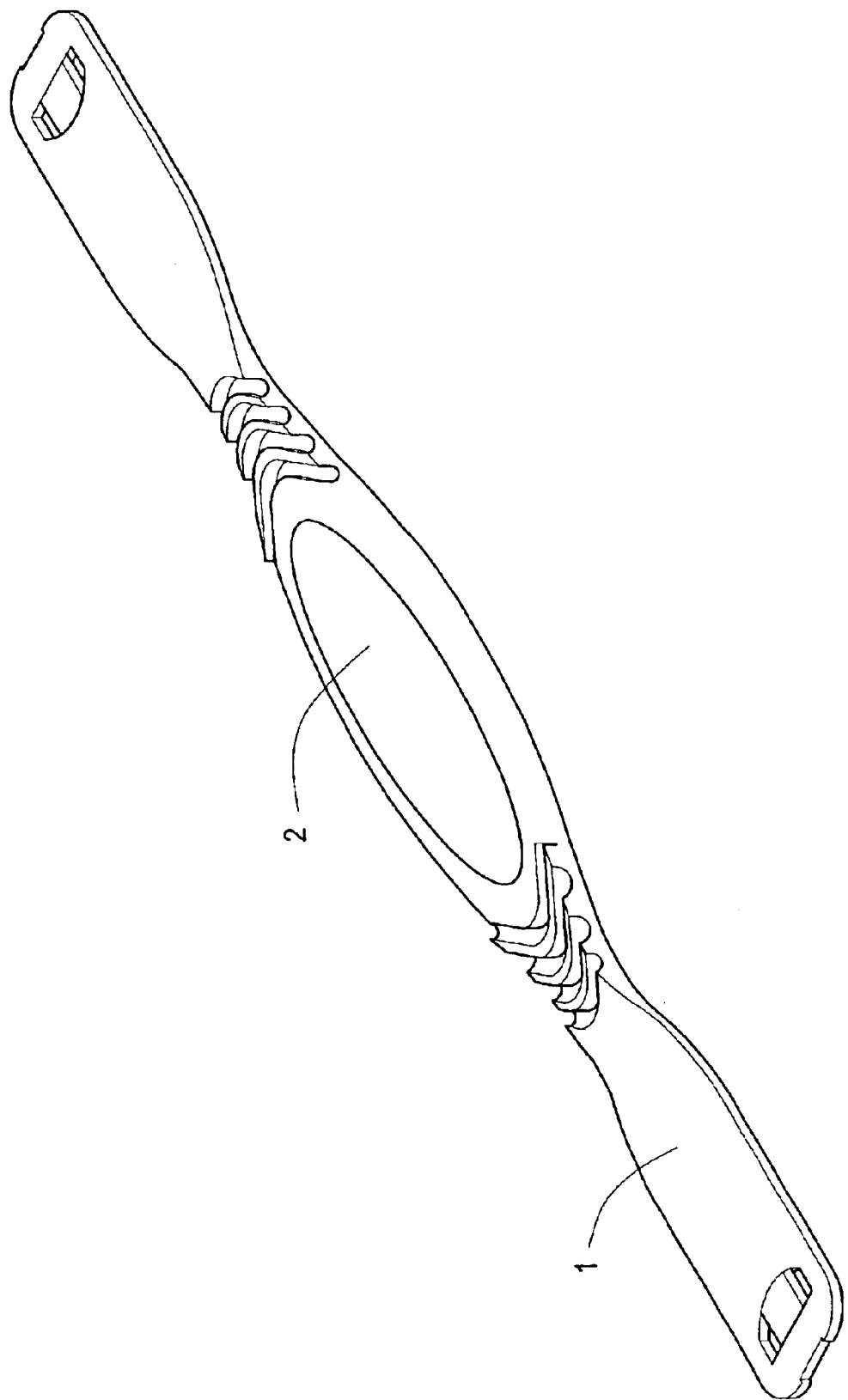
FIG. 1 is a perspective of the present invention.
Figure 2:
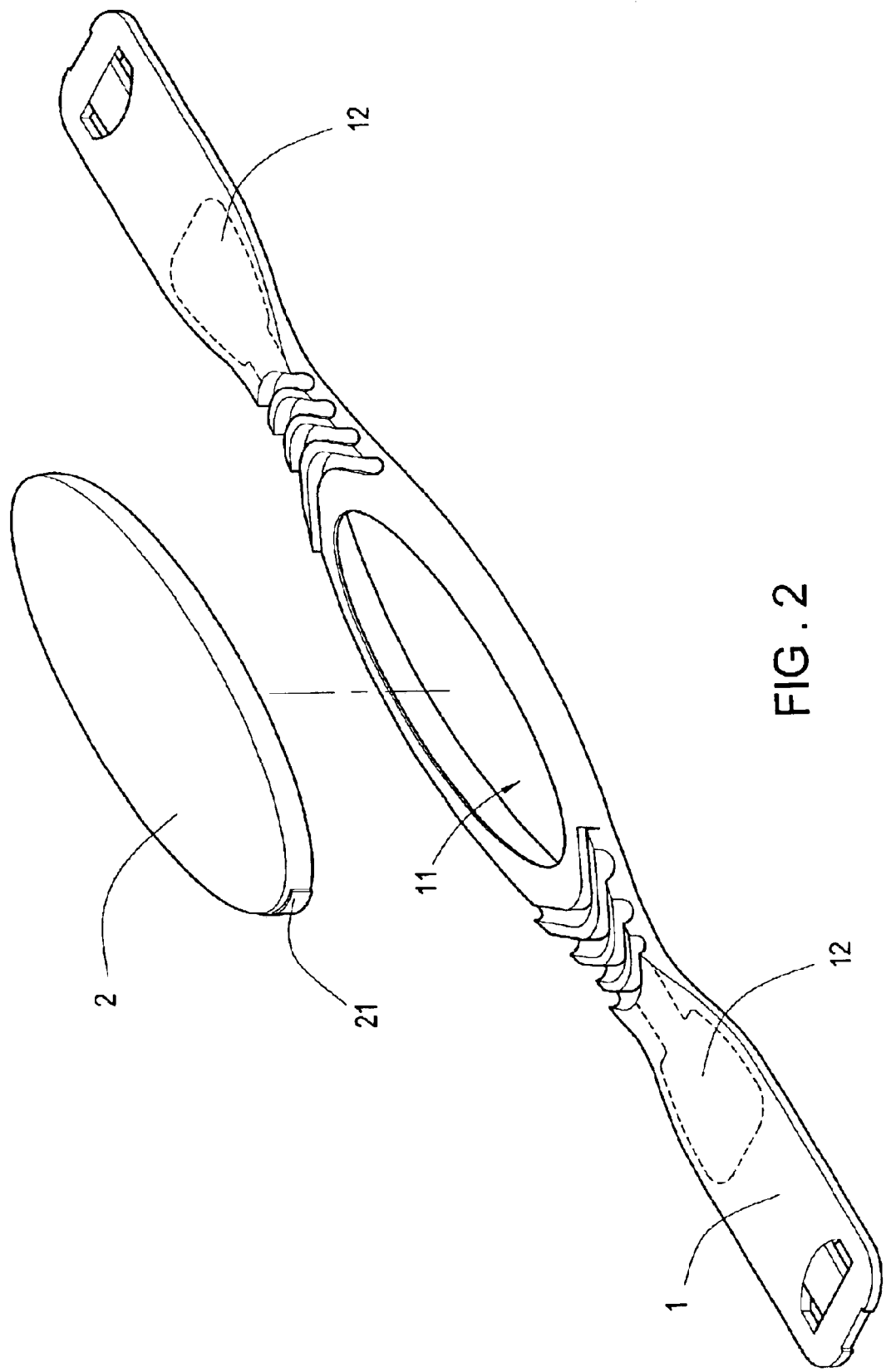
FIG. 2 is an assembly view of the present invention.
Figure 3:
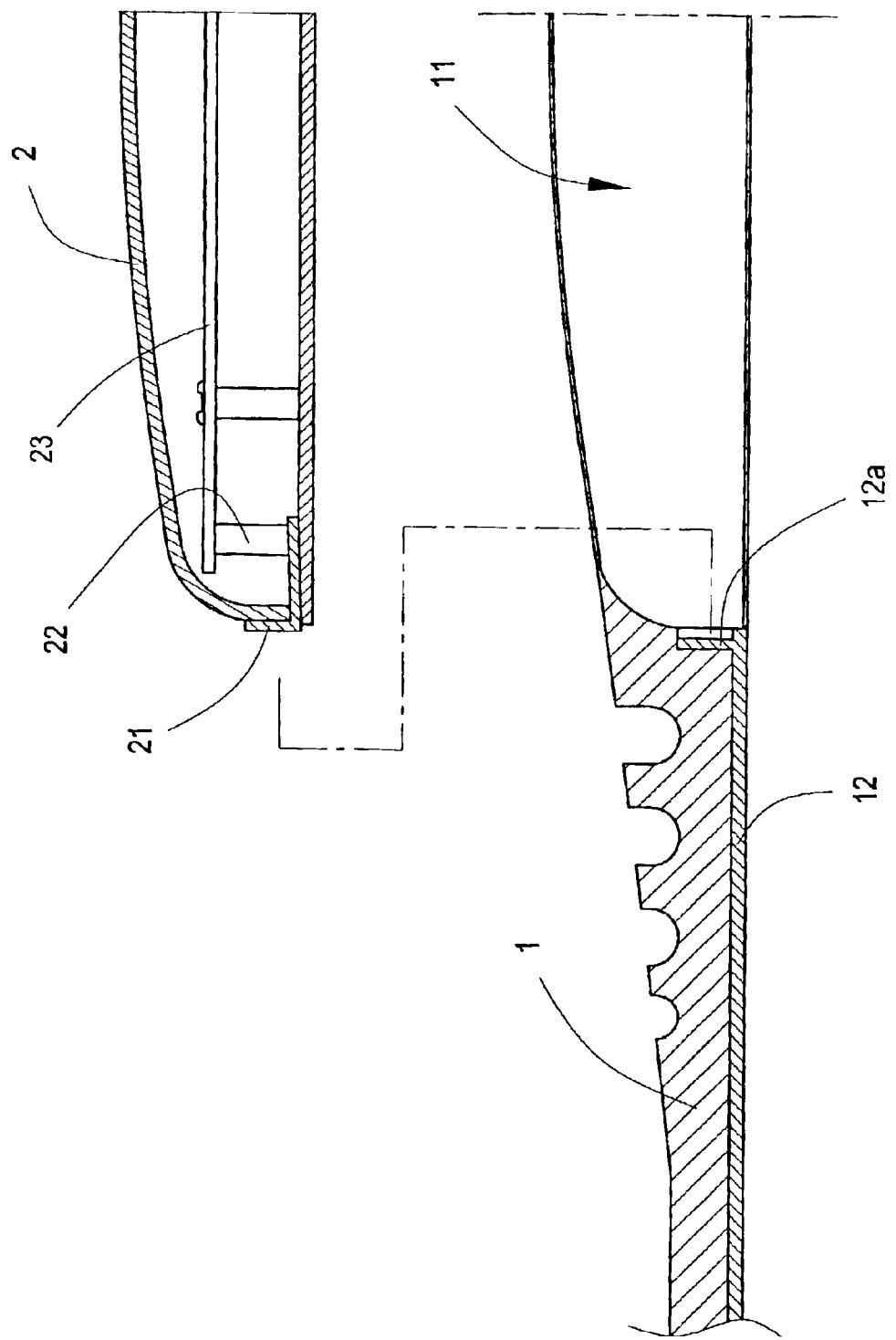
FIG. 3 is a cross-sectional of the present invention.
Figure 4:
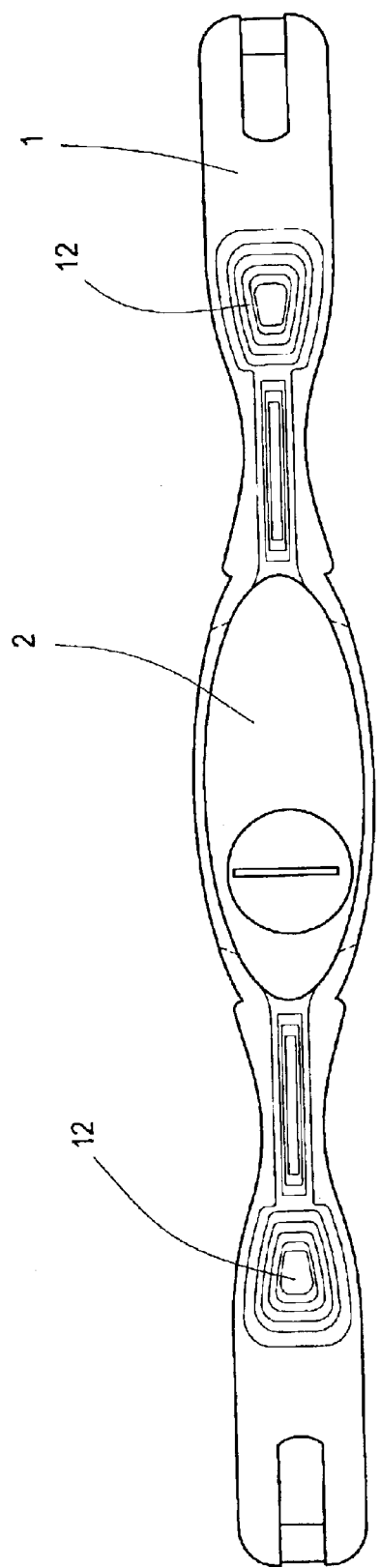
FIG. 4 is a bottom view of the present invention.

Referring to FIG. 1, FIG. 2 and FIG. 3, the present invention is composed of a strap (1) and a body (2). The functions of each component are described below:

The strap (1) is in long belt shape, a hole (11) is in the center of the strap (1), a conducting rubber plate (12) each is on both ends of the hole (11) of the strap (1), as shown in FIG. 4, a contacting tip (12a) stretches out from the conducting rubber plate (12) to the inner side of the hole (11).

Figure 5:
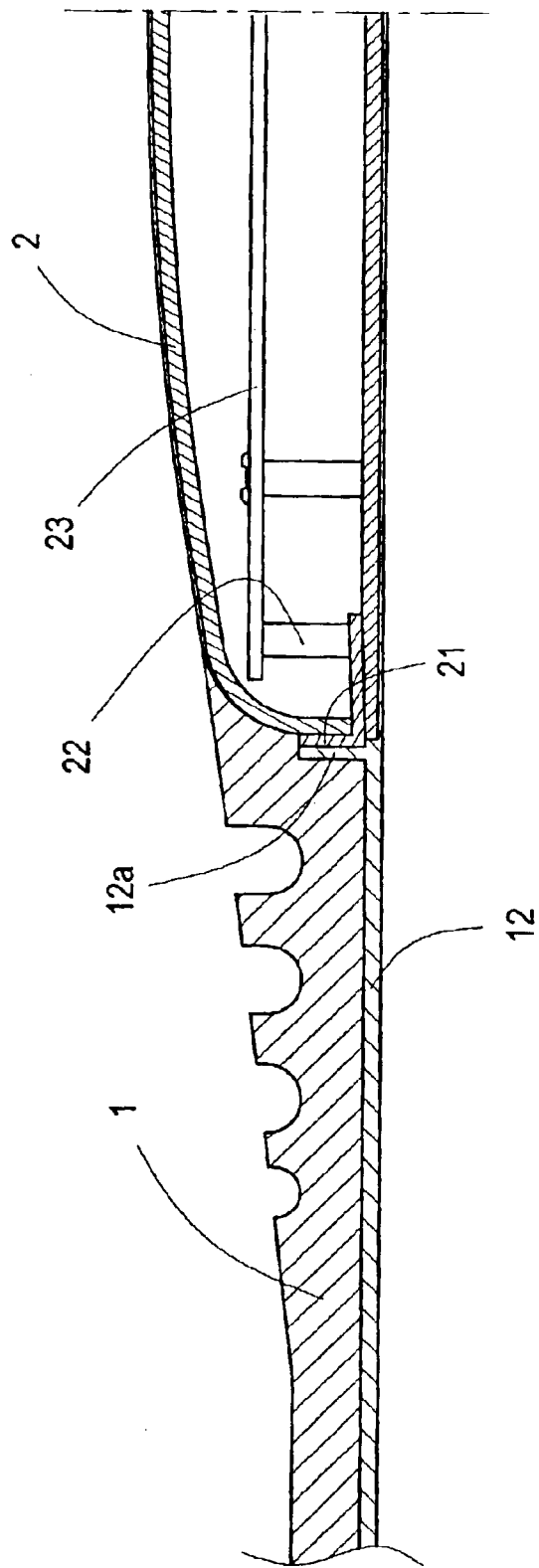
FIG. 5 is a cross-sectional assembly view of the present invention.
Figure 6:
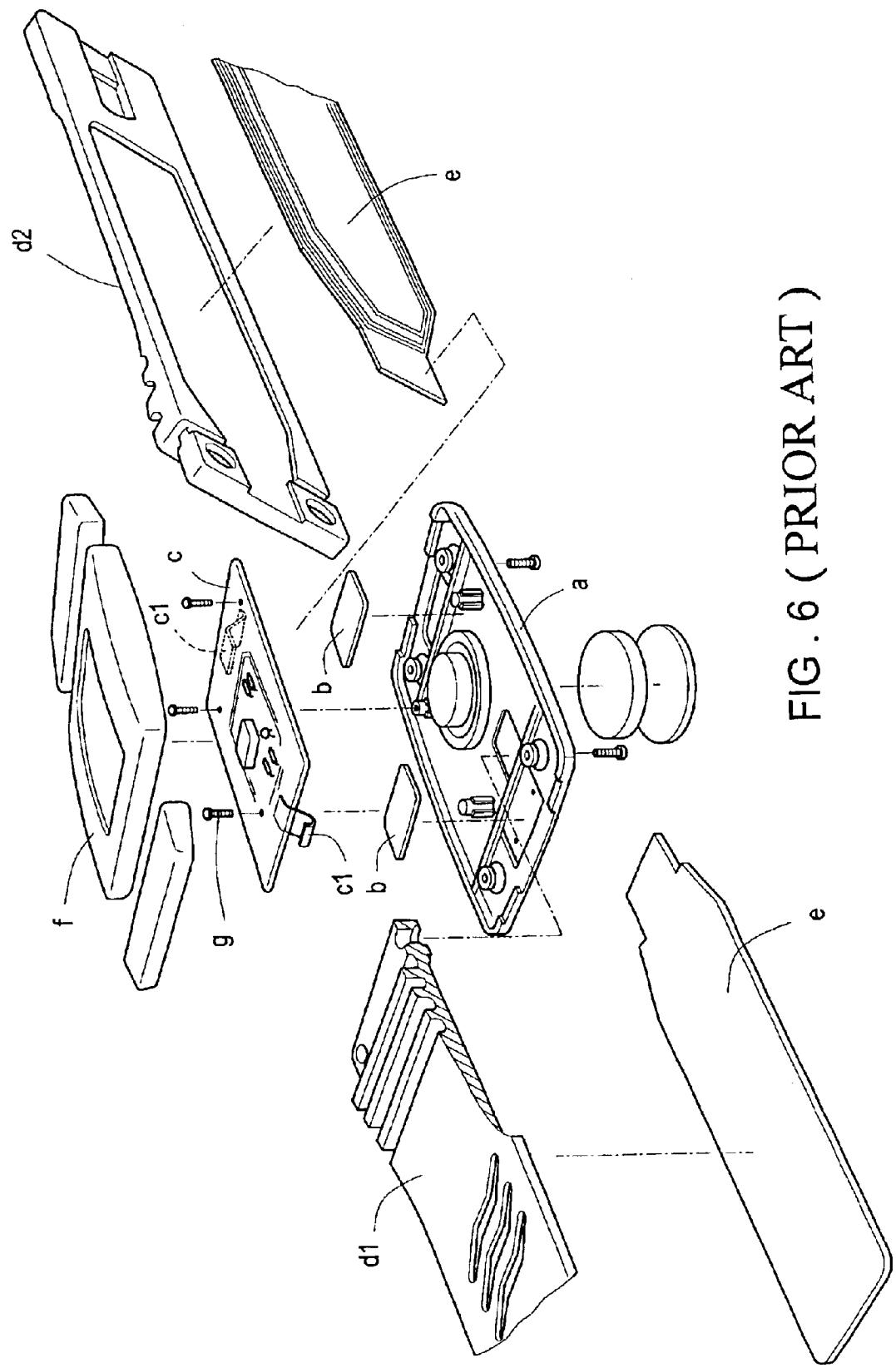
FIG. 6 is an assembly view of the prior art.
Figure 7:
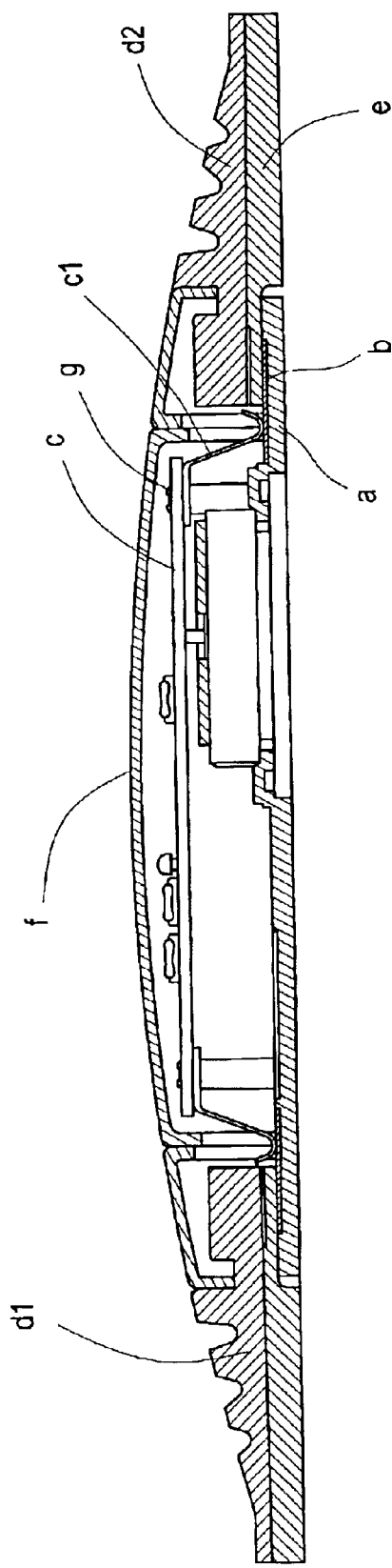
FIG. 7 is a cross-sectional of the prior art.

The body (2) is installed inside the hole (11) of the strap (1), two contacting point (21) are on both ends of the body (2); when the body (2) is inserted into the hole (11) of the strap (1), two contacting point (21) are pressed to contact the contacting tip (12a) of the conducting rubber plate (12) inside the hole (11) of the strap (1), as shown in FIG. 3; the contacting point (21) of the body (2) can contact the conducting rubber plate (12), as shown in FIG. 5, the conducting rubber plate (12) contacts human body to measure the heartbeat rate.

Based on above structure, the strap (1) has a hole (11) on center, users can insert the body (2) into the hole (11) to fastener the body (2) firmly to the strap (1), such mechanism can avoid the inconvenience and troublesome to apply tools for assembly, this method can achieve faster manufacturing process and lower manufacturing cost for better competition in the market.

After the body (2) is inserted into the hole (11) of the strap, the contacting point (21) of the body (2) can contact the contacting tip (12a) of the conducting rubber plate (12) inside the hole (11) to avoid the application tools as the prior arts to assemble the body (2) and the conducting rubber plate (12). The elasticity of the strap (1) can make the contacting tip (12a) of the conducting rubber plate (12) and the contacting point (21) of the body (2) contact firmly, as shown in FIG. 5, to avoid the bad connection condition.

The contacting point (21) of the body (2) contacts the circuit board (23) of the body (2) through a conductor (22), after the body (2) is inserted into the strap (1), the contacting point (21) is pressed firmly to contact the contacting tip (12a) on the end of the conducting rubber plate (12) inside the hole (11) of the strap (1); as shown in FIG. 5, the contacting point (21) of the body (2) can contact the conducting rubber plate (12). When the conducting rubber plate (12) touches the human body the present invention can measure the heartbeat rate.

As is seen in FIG. 3, the contacting tip 12a of the conducting rubber plate 12 extends generally perpendicular to a length of the conducting rubber plate 12 and is also generally perpendicular to a length of the strap 1, it is inset from an extreme end of the conducting rubber plate 12, and is not within the hole 11.

While a preferred embodiment of the invention has been shown and described in detail, it will be readily understood and appreciated that numerous omissions, changes and additions may be made without departing from the spirit and scope of the invention.

What is claimed is:

1. A heart rate transmitter comprising:
    a strap shaped as a single long belt including a hole in the center of said strap, said strap further comprising at least one conducting rubber plate extending along a length of said strap from said hole, and a contacting tip of said conducting rubber plate that stretches out from said conducting rubber plate adjacent to the inner side of said hole;
    a body installed inside said hole of said strap, said body comprising at least one electrical contacting point at a periphery of said body to connect said contacting tip of said conducting rubber plate when said body is inserted into said hole of said strap; and
    a transmitter device comprised of said body.

2. The heart rate transmitter according to claim 1, wherein said contacting tip of said conducting rubber plate extends generally perpendicular to a length of said conducting rubber plate.

3. The heart rate transmitter according to claim 2, wherein said contacting tip of said conducting rubber plate is inset from an extreme end of said conducting rubber plate.

4. The heart rate transmitter according to claim 2, wherein said contacting tip of said conducting rubber plate is not within said hole.

5. The heart rate transmitter according to claim 1, wherein said contacting tip of said conducting rubber plate extends generally perpendicular to a length of said strap.

6. The heart rate transmitter according to claim 1, wherein said strap is integral.

7. The heart rate transmitter according to claim 1, comprising two straps.

* * * * *